United States Patent [19]

Shigematsu et al.

[11] Patent Number: 4,969,949
[45] Date of Patent: Nov. 13, 1990

[54] PYRIMIDINE DERIVATIVES, PROCESSES FOR THEIR PRODUCTION AND HERBICIDAL COMPOSITIONS CONTAINING THEM

[75] Inventors: Masahiro Shigematsu, Shizuoka; Shoji Kusano, Hamamatsu; Takayoshi Takehi; Takeshige Miyazawa, both of Shizuoka; Yasufumi Toyokawa, Tokyo, all of Japan

[73] Assignees: Kumiai Chemical Industry Co., Ltd.; Ihara Chemical Industry Co., Ltd., both of Tokyo, Japan

[21] Appl. No.: 326,638

[22] Filed: Mar. 21, 1989

[30] Foreign Application Priority Data

Mar. 31, 1988 [JP] Japan ................................. 63-79921

[51] Int. Cl.$^5$ .................... C07D 403/12; A01N 43/54
[52] U.S. Cl. ........................ 71/92; 544/300; 546/298
[58] Field of Search ........................... 71/92; 544/300; 546/298

[56] References Cited

U.S. PATENT DOCUMENTS 4,190,656  2/1980  Matsumaura et al. ............ 544/300

*Primary Examiner*—John M. Ford
*Attorney, Agent, or Firm*—Oblon, Spivak, McClelland, Maier & Neustadt

[57] ABSTRACT

A pyrimidine derivative of the formula:

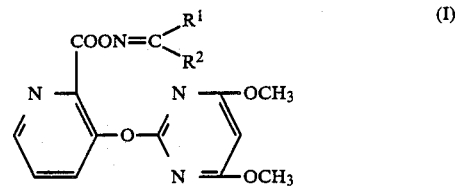

wherein each of $R^1$ and $R^2$ which may be the same or different is an alkyl group, or $R^1$ and $R^2$ together with the adjacent carbon atom form a ring.

4 Claims, No Drawings

PYRIMIDINE DERIVATIVES, PROCESSES FOR THEIR PRODUCTION AND HERBICIDAL COMPOSITIONS CONTAINING THEM

The present invention relates to novel pyrimidine derivatives and herbicidal compositions containing them as active ingredients applicable to paddy fields, upland fields or non-agricultural fields.

U.S. Pat. No. 4,427,437 and Agr. Biol. Chem., Vol. 30, No. 9, p. 896 (1966) disclose that pyrimidine derivatives have herbicidal activities.

However, the compounds disclosed in these references have a drawback that their herbicidal activities are inadequate, or they have low safety to some crop plants although the herbicidal activities are high.

The present inventors have conducted extensive researches with an aim to develop a compound having excellent herbicidal activities and high safety to crop plants, and have found that the compounds of the present invention exhibit excellent herbicidal activities against not only annual weeds but also perennial weeds such as quackgrass (*Agropyron repens*) and Johnsongrass (*Sorghum halepense*), and they are highly safe to crop plants, particularly to corn. The present invention has been acomplished on the basis of these discoveries.

The present invention provides a pyrimidine derivative of the formula:

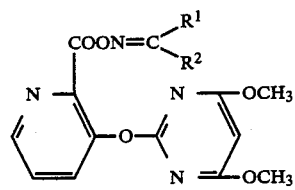
(I)

wherein each of $R^1$ and $R^2$ which may be the same or different is a straight chain or branched alkyl group, preferably a $C_1$–$C_6$ alkyl, more preferably a $C_1$–$C_3$ alkyl, or $R^1$ and $R^2$ together with the adjacent carbon atom form a ring, preferably a $C_3$–$C_7$ ring, more preferably a $C_4$–$C_5$ ring.

The present invention also provides a herbicidal composition comprising a herbicidally effective amount of a pyrimidine derivative of the formula I, and a carrier.

Further, the present invention provides a process for producing a pyrimidine derivative of the formula I which comprises reacting 3-hydroxypicolinic acid with an oxime of the formula:

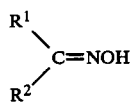
(V)

wherein $R^1$ and $R^2$ are as defined above, in a solvent in the presence of a condensing agent or a halogenating agent, and a base, to prepare an alkylidenamino ester of 3-hydroxypicolinic acid of the formula:

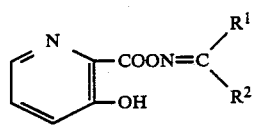
(II)

wherein $R^1$ and $R^2$ are as defined above, and reacting the ester with a 2,4,6-trisubstituted pyrimidine of the formula:

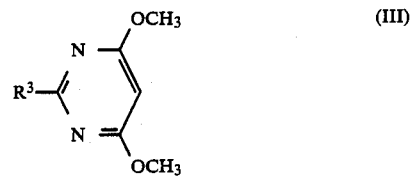
(III)

wherein $R^3$ is a halogen atom, an alkylsulfonyl group, a benzylsulfonyl group or a substituted benzylsulfonyl group in the presence of a base.

The hydroxypicolinic acid derivative of the formula II as an intermediate compound in this process is a novel compound. Such compound and a process for its production are also within the scope of the present invention. The present invention provides another process for producing a pyrimidine derivative of the formula I, which comprises reacting 3-(4,6-dimethoxypyrimidin-2-yl)oxypicolinic acid with an oxime of the formula:

(V)

wherein $R^1$ and $R^2$ are as defined above, in a solvent in the presence of a condensing agent or a halogenating agent, and a base.

Now, typical examples of the compound of the present invention will be presented in Table 1. Compound Nos. given in Table 1 will be referred to in the subsequent description in the specification. When $R^1$ and $R^2$ are different from each other, the product is a mixture of the syn-isomer and the anti-isomer.

TABLE 1

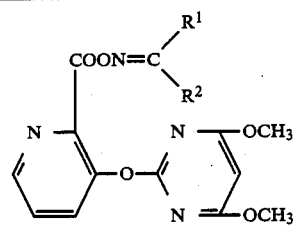

| Compound No. | $R^1$ | $R^2$ | Melting point (°C.) or Refractive index ($n_D^{20}$) |
|---|---|---|---|
| 1 | CH₃ | CH₃ | 123–126° C. |
| 2 | C₂H₅ | C₂H₅ | 134.5–137.5 |
| 3 | n-C₃H₇ | n-C₃H₇ | 67–68 |
| 4 | iso-C₃H₇ | iso-C₃H₇ | 117–117.5 |
| 5 | n-C₄H₉ | n-C₄H₉ | 1.5324 |
| 6 | —(CH₂)₄— | | 111–112 |
| 7 | —(CH₂)₅— | | 106–106.5 |
| 8 | CH₃ | C₂H₅ | 105–106.5 |
| 9 | CH₃ | iso-C₃H₇ | 89–92 |
| 10 | C₂H₅ | n-C₃H₇ | 109–111 |

The compound of the present invention can be prepared by the following processes.

PROCESS A

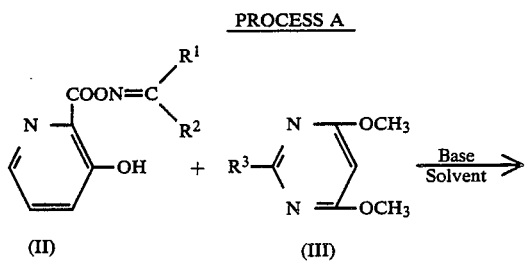 + 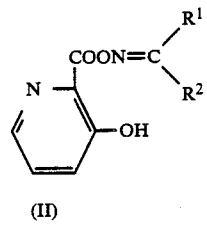 $\xrightarrow[\text{Solvent}]{\text{Base}}$

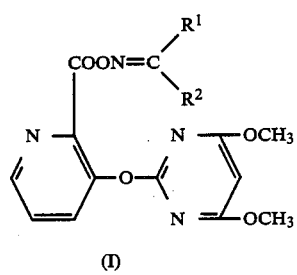

(I)

In the above formulas, $R^1$, $R^2$ and $R^3$ are as defined The compound of the formula I can be prepared by reacting the compound of the formula II with the pyrimidine compound of the formula III in the presence of a base, preferably in a solvent, at a temperature within a range of from room temperature to the boiling point of the solvent for from 1 to 24 hours. As the base an alkali metal such as sodium metal or potassium metal, an alkali metal or alkaline earth metal hydride such as sodium hydride, potassium hydride or calcium hydride, a carbonate such as sodium carbonate or potassium carbonate, or a metal hydroxide such as sodium hydroxide or potassium hydroxide, may be employed.

As the solvent, a hydrocarbon solvent such as benzene, toluene or xylene, a halogenated hydrocarbon solvent such as methylene chloride or chloroform, an alcohol solvent such as methanol, ethanol or isopropyl alcohol, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic solvent such as N,N-dimethylformamide, N,N-dimethylacetamide or dimethylsulfoxide, acetonitrile, or water, may be mentioned.

When the reaction is conducted in the absence of a solvent, the compound of the present invention can be prepared by conducting the reaction in the presence of a base, for example, an alkali metal carbonate such as anhydrous potassium carbonate at a temperature within a range of from 120° to 160° C.

The compound of the formula II can be prepared by the following process.

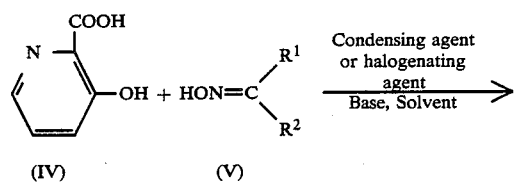 $\xrightarrow[\text{Base, Solvent}]{\text{Condensing agent or halogenating agent}}$ (IV)    (V)

-continued

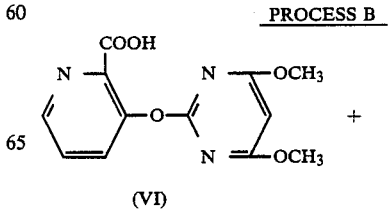

(II)

In the above formulas, $R^1$ and $R^2$ are as defined above.

Namely, the compound of the formula II can be prepared by reacting the compound of the formula IV with the compound of the formula V in the presence of a base, preferably in a solvent, at a temperature within a range of from $-50°$ C. to the boiling point of the solvent by using a condensing agent or a halogenating agent for from 1 to 24 hours.

Here, the base includes an organic base and an inorganic base. As the organic base, triethylamine or pyridine may be mentioned. As the inorganic base, an alkali metal such as sodium metal or potassium metal, an alkali metal or alkaline earth metal hydride such as sodium hydride, potassium hydride or calcium hydride, or a carbonate such as lithium carbonate, sodium carbonate, potassium carbonate, sodium hydrogencarbonate or potassium hydrogencarbonate, may be mentioned.

As the solvent, a hydrocarbon solvent such as benzene, toluene or xylene, a halogenated hydrocarbon solvent such as methylene chloride or chloroform, a ketone solvent such as acetone or methyl ethyl ketone, an ester solvent such as methyl acetate or ethyl acetate, an alcohol solvent such as methanol, ethanol or isopropyl alcohol, an ether solvent such as ethyl ether, isopropyl ether, tetrahydrofuran or 1,4-dioxane, an aprotic solvent such as N,N-dimethylformamide, N,N-dimethylacetamide, dimethylsulfoxide or hexamethylphosphoric acid triamide, or acetonitrile may be employed. As the condensing agent, a halogenated organophosphorus compound such as diethyl chlorophosphate, diethyl bromophosphate, phenyl dichlorophosphate, diphenyl chlorophosphate, dichloro-N,N-dimethyl phosphoric acid amide, chlorophenyl-N-phenylphosphoric acid amide or chloro-N,N-bis(2-oxo-3-oxazolidinyl)phosphenic acid, N,N-dicyclohexylcarbodiimide, or N,N-carbonyldiimidazole, may be employed. As the halogenating agent, thionyl chloride, oxalyl chloride, sulfuryl chloride, phosphorus oxychloride, phosphorus trichloride, phosphorus pentachloride or phosphorus tribromide, may be employed.

In the above process, instead of the compound of the formula V, an alkali metal or alkaline earth metal salt thereof may be used.

PROCESS B

COOH (VI)

-continued
PROCESS B

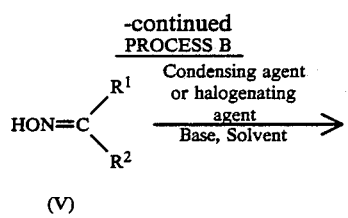

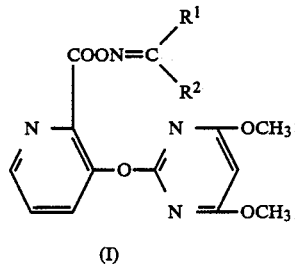

In the above formulas, R¹ and R² are as defined above.

Namely, the compound of the formula I of the present invention can also be prepared by reacting the compound of the formula VI with the compound of the formula V in the presence of a base, preferably in a solvent, at a temperature within a range of from −50° C. to the boiling point of the solvent by using a condensing agent or a halogenating agent for from 1 to 24 hours.

Here, the base, the solvent, the condensing agent and the halogenating agent may be the same as above used in Process A.

Now, the processes of the present invention will be described in further detail with reference to Examples and Reference Example. However, it should be understood that the present invention is by no means restricted to such specific Examples.

EXAMPLE 1

Preparation of 5-nonanylideneamino 3-(4,6-dimethoxypyrimidin-2-yl)oxypicolinate (Compound No. 5)

To a mixture of 6.3 g of 5-nonanylidenamino 3-hydroxypicolinate, 2.5 g of 2-methylsulfonyl-4,6-dimethoxypyrimidine and 3.9 g of anhydrous potassium carbonate, 50 ml of N,N-dimethylformamide was added, and the mixture was stirred at 100° C. for 2 hours. After cooling, the reaction solution was poured into water and extracted with ethyl ether. The organic layer was further washed with water and then dried over anhydrous sodium sulfate. The solvent was distilled off under reduced pressure, and the residue thereby obtained was purified by silica gel column chromatography by using as a developing solvent a mixture of hexane/ethyl ether to obtain 5.2 g of the above identified compound as slightly yellow transparent viscous liquid.

Refractive index ($n_D^{20}$): 1.5324

EXAMPLE 2

Preparation of isopropylidenamino 3-(4,6-dimethoxpyrimidin-2-yl)oxypicolinate (Compound No. 1)

3.0 g of 3-(4,6-dimethoxpyrimidin-2-yl)oxypicolinic acid, 3.96 g of acetoxime and 1.71 g of pyridine were dissolved in 20 ml of N,N-dimethylformamide, and then, 3.51 g of dichloro-N,N-dimethylphosphoric acid amide was dropwise added thereto or 0° C. After the dropwise addition, the mixture was stirred at room temperature for 3 hours to complete the reaction. The reaction solution was poured into water. Precipitated crystals were separated by filtration, then washed with water and dried to obtain 2.20 g of the above identified compound as white crystals.

Melting point: 123°–126° C.

REFERENCE EXAMPLE

Preparation of 3-pentylidenamino 3-hydroxypicolinate

To 7.0 g of 3 hydroxypicolinic acid, 10 ml of N,N-dimethylformamide was added, and then 5.9 g of thionyl chloride was dropwise added thereto at a temperature of at most 10° C. The mixture was stirred at 0° C. for 30 minutes. To the reaction solution, 30 ml of chloroform was added, and the mixture was further stirred at 0° C. for 15 minutes. Then, a solution prepared by dissolving 5.0 g of diethyl ketone oxime in 50 ml of chloroform was dropwise added thereto at 0° C., and the mixture was stirred for 30 minutes. Then, 7.9 g of pyridine was dropwise added thereto. Then, the reaction solution was stirred at 0° C. for one hour and at room temperature for one day. The reaction solution was poured into water and extracted with ethyl acetate. Then, the extract was washed with a saturated sodium hydrogencarbonate aqueous solution and with a saturated sodium chloride aqueous solution and dried over anhydrous sodium sulfate. The solvent was distilled off under reduced pressure, and the residue thereby obtained was purified by silica gel column chromatography by using as a developing solvent a mixture of hexane/ethyl ether to obtain 6.5 g of the above identified compound as slightly yellow transparent viscous liquid.

Refractive index ($n_D^{20}$): 1.5370

The compounds useful as starting materials for the process for producing the compounds of the present invention, prepared in accordance with Reference Example, are shown in Table 2. When R¹ and R² are different from each other, the product is a mixture of the syn-isomer and the anti-isomer.

TABLE 2

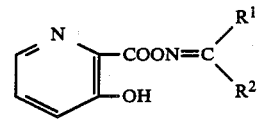

| Compound No. | R¹ | R² | Melting point (°C.) or Refractive index ($n_D^{20}$) |
|---|---|---|---|
| 11 | CH₃ | CH₃ | 80–82 |
| 12 | C₂H₅ | C₂H₅ | 1.5370 |
| 13 | n-C₃H₇ | n-C₃H₇ | 1.5249 |
| 14 | iso-C₃H₇ | iso-C₃H₇ | 51–56 |
| 15 | n-C₄H₉ | n-C₄H₉ | 1.5162 |
| 16 | —(CH₂)₄— | | 68–74 |
| 17 | —(CH₂)₅— | | 1.5681 |
| 18 | CH₃ | C₂H₅ | 1.5470 |
| 19 | CH₃ | iso-C₃H₇ | 1.5378 |
| 20 | C₂H₅ | n-C₃H₇ | 1.5244 |

The herbicidal composition of the present invention comprises a herbicidally effective amount of the pyrimidine derivative of the present invention and a carrier.

The herbicide of the present invention may be used as it is or may be formulated in various formulations which are commonly used as herbicidal compositions, such as a wettable powder, a granule, an emulsifiable concentrate or a dust by blending it with a carrier, surfactant, a dispersing agent or an ajuvant which is commonly employed for the formulation of agricultural chemicals.

As the carrier to be used for the formulation, there may be mentioned a solid carrier such as Jeeklight, talc, bentonite, cray, Kaolin, diatomaceous/earth, white carbon, vermiculit, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethylcellurose, polyethylene glycol or gum arabic may be mentioned. The herbicide may be diluted to a suitable concentration before application, or may directly be applied.

Further, the herbicide of the present invention may be used in combination with other herbicides.

The herbicide of the present invention is capable of controlling various weeds in an upland field by soil treatment before or after the emergence of weeds or by foliage treatment. Further, the herbicide is capable of controlling various weeds in a paddy field by irrigated soil treatment before or after the emergence of weeds or by foliage treatment. The herbicide of the present invention is applied in a dose of from 0.1 g to 1 kg, preferably from 1 to 400 g, more preferably from 1 to 100 g, of the active ingredient per 10 ares. For foliage treatment, it is diluted to a concentration of from 1 to 10,000 ppm for application. The concentration for foliage treatment substantially varies depending upon the spraying method e.g. whether it is by an airplane, by a tractor or by a manual means.

Among the compounds of the present invention, Compound Nos. 1, 2, 3 and 6 exhibit particularly excellent herbicidal activities.

Now, Formulation Examples for the herbicidal composition of the present invention will be given. However, it should be understood that the present invention is by no means restricted to these specific Formulation Examples. In these Examples, "%" means "% by weight".

FORMULATION EXAMPLE 1 (wettable powder)

10% of Compound No. 1, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (trademark, Jeeklite Company Ltd.) were uniformly mixed and pulverized to obtain a wettable powder.

FORMULATION EXAMPLE 2 (emulsifiable concentrate)

30% of Compound No. 1, 20% of cyclohexanone, 11% of a polyoxyethylene alkyl aryl ether, 4% of a calcium alkylbenzenesulfonate and 35% of methyl naphthalene, were uniformly dissolved to obtain an emulsifiable concentrate.

FORMULATION EXAMPLE 3 (granule)

5% of Compound No. 1, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4 (dust)

2% of Compound No. 1, 5% of diatomaceous earth and 93% of clay were uniformly mixed and pulverized to obtain a dust.

The compounds and the herbicidal compositions of the present invention ar capable of effectively controlling annual weeds such as barnyardgrass (*Echinochloa crusgalli*), crabgrass (*Diqitaria sanguinalis*), goosegrass (*Eleusine indica*), green foxtail (*Setaria viridis*), giant foxtail (*Setaria faberi*), yellow foxtail (*Setaria glauca*), shattercane (*Sorghum bicolor*), proso millet (*Panicum miliaceum*), fall panicum (*Panicum dichotomiflorum*), itchgrass (*Rottoboelia exaltata*), downy brome (*Bromus tectorum*), water foxtail (*Alopecurus aequalis*), annual bluegrass (*Poa annua*), wild oat (*Avena fatua*), italian ryegrass (*Lolium multiflorum*), pale smartweed (*Polygonum lapathifolium*), slender amaranth (*Amaranthus viridis*), lambsquarters (*Chenopodium album*), velvetleaf (*Abutilon theophrasti*), common cocklebur (*Xanthium strumarium*), morningglory (*Ipomea spp*), chickweed (*Stellaria media*), prickly sida (*Sida spinosa*), sicklepod (*Cassia tora*), *Calystegia hederacea*, wild mustard (*Brassica arvensis*), *Calystegia arevensis*, jimsonweed (*Datura stamonium*), rice flatsedge (*Cyperus iria*), broadleaf signalgrass (*Brachiaria platyphylla*), wild buckwheat (*Polygonum convolvulus*), and devils beggarticks (*Bidens frondosa*), and perennial weeds such as purple nutsedge (*Cyperus rotundus*), johnsongrass (*Sorghum halepense*), bermudagrass (*Cynodon dactylon*) and quackgrass (*Ahropyron repens*) grown in upland fields. Further, they are capable of effectively controlling annual weeds such as barnyardgrass (*Echinochloa crusgalli*), flatsedge (*Cyperus difformis*), monochoria (*Monochoria vaginalis*), bulrush (*Scirpus hotarui*) and *Alisma canaliculatum*, and perennial weeds such as *Cyperus serotinus*, *Sagittaria pygmaea* and *Eleocharis kuroguwai*, grown in paddy fields. On the other hand, they are highly safe to crop plants, particularly corn.

Now, the herbicidal activities of the herbicides of the present invention will be described with reference to Test Examples.

The following abbreviations represent the following test plants:

Ec: barnyardgrass, Di: crabgrass,
Po: smartweed, Am: slender amaranth,
Ch: lambsquarters, Cy: rice flatsedge,
Se: green foxtail, Ip: morningglory,
Xa: common cocklebur, So: Johnsongrass,
Al: blackgrass, Ab: velvetleaf and Ze: corn The following compounds were used as comparative compounds.

COMPARATIVE COMPOUND A:

Ehtyl 3-(5-chloropyrimidin-2-yloxy)benzoate (which is a compound disclosed in Japanese Unexamined Patent Publication No 55729/1979)

COMPARATIVE COMPOUND B:

2-tolyloxy-4,6-dimethylpyrimidine (which is a compound disclosed in Agr. Biol. Chem., Vol. 30, No. 9, p. 896)

TEST EXAMPLE 1

In a pot filled with soil (surface area: 100 cm$^2$), seeds of barnyardgrass (Ec), crabgrass (Di), smartweed (Po), slender amaranth (Am), lambsquarters (Ch) and rice flatsedge (Cy), were sown and covered with soil in a thickness of from 0.5 to 1 cm. The pot was cultured in a green house at a temperature of from 20° to 25° C. for 2 weeks, and then a predetermined amount of a wettable powder prepared in accordance with Formulation Example 1 was diluted with water, and applied to the foliage at a rate of 100 liters per 10 ares so that the dose of active ingredient was 100 g/10 ares. The evaluation was conducted on the 14th day after the treatment in accordance with the standard as identified in Table 3. The results are shown by the index numbers in Table 4.

TABLE 3

| Index No. | Herbicidal effects |
|---|---|
| 0 | No herbicidal effect |
| 1 | Herbicidal effect: more than 0% and less than 30% |
| 2 | Herbicidal effect: at least 30% and less than 50% |
| 3 | Herbicidal effect: at least 50% and less than 70% |
| 4 | Herbicidal effect: at least 70% and less than 90% |
| 5 | Herbicidal effect: more than 90% |

TABLE 4

| Compound No. | Ec | Di | Po | Am | Ch | Cy |
|---|---|---|---|---|---|---|
| 1 | 5 | 5 | 5 | 5 | 5 | 5 |
| 2 | 5 | 4 | 4 | 5 | 5 | 5 |
| 3 | 5 | 5 | 5 | 5 | 5 | 5 |
| 4 | 5 | 4 | 5 | 5 | 5 | 5 |
| 5 | 5 | 5 | 5 | 5 | 5 | 5 |
| 6 | 5 | 5 | 5 | 5 | 5 | 5 |
| 7 | 5 | 5 | 5 | 5 | 5 | 5 |
| 8 | 5 | 5 | 5 | 5 | 5 | 5 |
| 9 | 5 | 5 | 5 | 5 | 5 | 5 |
| 10 | 5 | 5 | 5 | 5 | 5 | 5 |
| Comparative | | | | | | |
| Compound A | 0 | 1 | 1 | 1 | 0 | 1 |
| Compound B | 0 | 0 | 0 | 0 | 0 | 0 |

TEST EXAMPLE 2

In a pot filled with soil (surface area: 100 cm$^2$), seeds of barnyardgrass (Ec), crabgrass (Di), smartweed (Po), slender amaranth (Am), lambsquarters (Ch) and rice flatsedge (Cy) were sown and covered with soil in a thickness of from 0.5 to 1 cm. One day later from the seeding, a predetermined amount of a wettable powder prepared in accordance with Formulation Example 1, was diluted with water and applied to the soil surface at a rate of 100 liters per 10 ares so that the dose of active ingredient was 100 g/10 ares. The evaluation was conducted on the 20th day after the treatment in accordance with the standard as identified in Table 3. The results are shown by the index numbers in Table 5.

TABLE 5

| Compound No. | Ec | Di | Po | Am | Ch | Cy |
|---|---|---|---|---|---|---|
| 1 | 5 | 5 | 5 | 5 | 5 | 5 |
| 2 | 5 | 4 | 5 | 5 | 5 | 5 |
| 3 | 4 | 4 | 5 | 4 | 5 | 5 |
| Comparative | | | | | | |
| Compound A | 0 | 0 | 0 | 0 | 0 | 0 |
| Compound B | 0 | 0 | 0 | 0 | 0 | 0 |

TEST EXAMPLE 3

In a pot filled with soil (surface area: 600 cm$^2$), seeds of barnyardgrass (Ec), crabgrass (Di), green foxtail (Se), blackgrass (Al), smartweed (Po), slender amaranth (Am), lambsquaters (Ch), velvetleaf (Ab), morningglory (Ip), common cocklebur (Xa) and corn (Ze) were sown, and tubers of Johnsongrass (So) were planted. The pot was cultured in a green house until corn grew to the 3 or 4 leaf stage, and then, a predetermined amount of a wettable powder prepared in accordance with Formulation Example 1 was diluted with water, and applied to the foliage of the grown plants at a rate of 100 liters per 10 ares. The evaluations were conducted on the 30th day after the treatment with respect to the herbicidal effect in accordance with the standard as identified in Table 3 and with respect to the phytotoxicity in accordance with the standard as identified in Table 6. The results are shown by the index numbers in Table 7.

TABLE 6

| Index No. | Phytotoxicity |
|---|---|
| 0 | No phytotoxicity |
| 1 | Phytotoxicity: more than 0% and less than 30% |
| 2 | Phytotoxicity: at least 30% and less than 50% |
| 3 | Phytotoxicity: at least 50% and less than 70% |
| 4 | Phytotoxicity: at least 70% and less than 90% |
| 5 | Phytotoxicity: more than 90% to completely withered |

TABLE 7

| Compound No. | Dose (g/10a) | Ec | Di | Se | So | Al | Po | Am | Ch | Ab | Ip | Xa | Phytotoxicity Ze |
|---|---|---|---|---|---|---|---|---|---|---|---|---|---|
| 1 | 100 | 5 | 5 | 5 | 5 | 5 | 5 | 5 | 5 | 5 | 5 | 5 | 1 |
| " | 25 | 5 | 4 | 5 | 5 | 5 | 5 | 5 | 5 | 5 | 4 | 5 | 0 |
| " | 6.3 | 5 | 4 | 5 | 5 | 5 | 4 | 5 | 5 | 5 | 3 | 4 | 0 |
| 2 | 100 | 5 | 5 | 5 | 5 | 5 | 5 | 5 | 5 | 5 | 5 | 4 | 0 |
| 3 | 25 | 5 | 5 | 5 | 5 | 5 | 5 | 5 | 5 | 5 | 5 | 5 | 0 |
| 5 | 25 | 5 | 5 | 5 | 5 | 5 | 5 | 5 | 5 | 5 | 4 | 4 | 1 |
| 6 | 25 | 5 | 5 | 5 | 5 | 5 | 5 | 5 | 5 | 5 | 4 | 5 | 1 |
| 7 | 25 | 5 | 4 | 5 | 5 | 5 | 5 | 5 | 5 | 5 | 4 | 5 | 1 |
| 8 | 6.3 | 5 | 4 | 5 | 5 | 4 | 5 | 5 | 5 | 5 | 4 | 4 | 0 |
| 10 | 25 | 5 | 3 | 5 | 5 | 5 | 5 | 5 | 5 | 5 | 4 | 4 | 0 |

We claim:
1. A pyrimidine derivative of the formula:

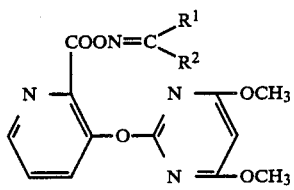

wherein each of $R^1$ and $R^2$ which may be the same or different is an alkyl group having from 1 to 6 carbon atoms, or $R^1$ and $R^2$ together with the adjacent carbon atom form a ring having from 3 to 7 carbon atoms.

2. The pyrimidine derivative according to claim 1, wherein the alkyl group for $R^1$ and $R^2$ is an alkyl group having from 1 to 3 carbon atoms.

3. A herbicical composition comprising a herbicidally effective amount of a pyrimidine derivative of the formula:

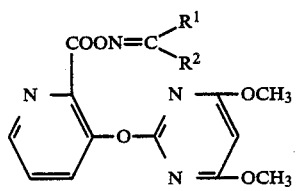

wherein each of $R^1$ and $R^2$ which may be the same or different is an alkyl group having from 1 to 6 carbon atoms, or $R^1$ and $R^2$ together with the adjacent carbon atom form a ring having from 3 to 7 carbon atoms, and a carrier.

4. A process for producing a pyrimidine derivative of the formula:

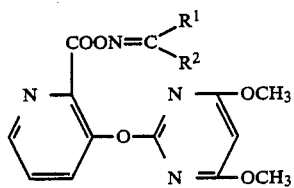

wherein each of $R^1$ and $R^2$ which may be the same or different is a straight chain or branched alkyl group having from 1 to 6 carbon atoms, or $R^1$ and $R^2$ together with the adjacent carbon atom form a ring having from 3 to 7 carbon atoms, which comprises reacting 3-hydroxypicolinic acid with an oxime of the formula:

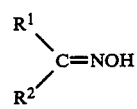

wherein $R^1$ and $R^2$ are as defined above, in a solvent in the presence of a condensing agent or halogenating agent, and a base, to prepare an alkylidenamino ester of 3-hydroxypicolinic acid of the formula:

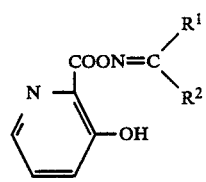

wherein $R^1$ and $R^2$ are as defined above, and reacting the ester with a 2,4,6-trisubstituted pyrimidine of the formula:

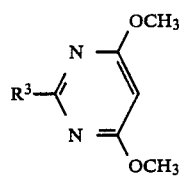

wherein $R^3$ is a halogen atom, an alkylsulfonyl group, a benzylsulfonyl group or a substituted benzylsulfonyl group in the presence of a base.

* * * * *